(12) United States Patent
Declerck et al.

(10) Patent No.: US 11,055,559 B1
(45) Date of Patent: Jul. 6, 2021

(54) SYSTEM, METHOD AND APPARATUS FOR ASSISTING A DETERMINATION OF MEDICAL IMAGES

(71) Applicant: Optellum Limited, Oxford (GB)

(72) Inventors: Jerome Declerck, Oxford (GB); Timor Kadir, Oxford (GB)

(73) Assignee: Optellum Limited, Oxford (GB)

( * ) Notice: Subject to any disclaimer, the term of this patent is extended or adjusted under 35 U.S.C. 154(b) by 0 days.

(21) Appl. No.: 16/755,171

(22) PCT Filed: Oct. 15, 2018

(86) PCT No.: PCT/EP2018/078121
§ 371 (c)(1),
(2) Date: Apr. 10, 2020

(87) PCT Pub. No.: WO2019/073086
PCT Pub. Date: Apr. 18, 2019

(30) Foreign Application Priority Data

Oct. 13, 2017 (GB) ..................................... 1716890

(51) Int. Cl.
*G06K 9/38* (2006.01)
*G06K 9/62* (2006.01)
*G16H 30/20* (2018.01)
*G06K 9/46* (2006.01)

(52) U.S. Cl.
CPC .............. *G06K 9/38* (2013.01); *G06K 9/4623* (2013.01); *G06K 9/6267* (2013.01); *G16H 30/20* (2018.01); *G06K 2009/4666* (2013.01); *G06K 2209/05* (2013.01)

(58) Field of Classification Search
None
See application file for complete search history.

(56) References Cited

U.S. PATENT DOCUMENTS

| 7,876,939 | B2 * | 1/2011 | Yankelevitz | A61B 6/03 382/128 |
| 10,890,641 | B2 * | 1/2021 | Wang | A61B 5/7203 |
| 2018/0268522 | A1 | 9/2018 | Hawkins et al. | |
| 2019/0087957 | A1 * | 3/2019 | Burris | A61B 6/5205 |

FOREIGN PATENT DOCUMENTS

WO 2005050563 A1 6/2005

OTHER PUBLICATIONS

3D General Lesion Segmentation in CT; Marie-Pierre Jolly and Leo Grady ; Siemens Corporate Research hnaging and Visualization Department Princeton, NJ, USA.

* cited by examiner

*Primary Examiner* — Fayyaz Alam
(74) *Attorney, Agent, or Firm* — Optimus Patents US, LLC

(57) ABSTRACT

A quantification system (300) is described that includes: at least one input (310) configured to provide at least one input medical image and provide a location of interest in the at least one input medical image; and a mapping circuit (325). The mapping circuit (325) is configured to: compute a direct quantification result from the location of interest of the at least one input medical image to a quantification of interest and output a direct first quantification result therefrom; generate a saliency map as part of the computation of the direct quantification result; and derive a segmentation from the saliency map, such that the segmentation independently generates a second quantification result that is within a result range of the direct first quantification result.

20 Claims, 8 Drawing Sheets

SYSTEM, METHOD AND APPARATUS FOR ASSISTING A DETERMINATION OF MEDICAL IMAGES

FIELD OF THE INVENTION

The field of this invention relates to Computer Aided Diagnostic (CADx) systems and methods for medical images, used to support clinicians in healthcare. In particular, the field relates to risk Computer Aided Diagnostic systems to assist the reading and reporting of medical images by radiologists and the interpretation of the radiologist's report by the physician responsible for patient care.

BACKGROUND OF THE INVENTION

In the field of medical imaging, a variety of technologies can be used to investigate biological processes and anatomy. Medical images are frequently used to support clinical decision making in many diseases. In the field of medical imaging, a variety of technologies can be used to investigate biological processes and anatomy. The following examples are types of scan that may be used to provide medical images: X-Ray; screening for lung cancer using Computed Tomography (CT); screening of women using mammography, Ultrasound (US); Magnetic Resonance Imaging (MRI); Single Photon Emission Tomography (SPECT); and Positron Emission Tomography (PET) that may be used to investigate functional changes that may be characteristic of disease. Each type of scan is referred to as an 'imaging modality'. It is known that CT and MRI may be used to investigate structural and morphological changes in anatomy that are indicative of disease.

Whether examining morphological or functional changes, the reading clinician, typically a radiologist, will often make a series of measurements on the medical images. For structural information, the clinician will make size, volume or angular measurements whereas for functional information the intensity of the image in regions of interest may be characteristic of disease. In some situations, both types of measurements are of interest.

Typically, a scan provides a 'dataset'. The dataset comprises digital information about the value of a variable at each of many spatial locations in either a two-dimensional or (more typically) a three-dimensional space. As a specific example, a CT scan may provide images of the chest of a patient. Such a CT scan might, as a more specific example, show lung nodules in the chest.

In some instances, a clinician is interested in changes to a measurement rather than its absolute value. For example, a growing lesion as seen on a CT scan of a screening subject may be indicative of a cancer. Hence measuring the change in lesion size, either as a single measurement of the longest single dimension in one plane or as a volumetric measurement can be used to quantify the magnitude of the change and likelihood of disease. Numerous guidelines recommend following patients in such a manner, for example the 'Guidelines for Management of Incidental Pulmonary Nodules Detected on CT Images', authored by the Fleischner Society 2017; and the 'British Thoracic Society guidelines for the investigation and management of pulmonary nodules' by the British Thoracic Society Standards of Care Committee. On a patient undergoing cancer therapy a reduction in the size or volume of a tumour may be indicative of a response to therapy and conversely an increase in size or volume may be suggestive of disease progression. Reduction in the brain grey matter as seen on an MRI may indicate progressive dementia.

Computer Aided Detection (CADe) systems are also known and aim to assist clinicians. CADe systems aim to provide a clinician with standardised, objective and repeatable information. That information might typically relate to structures, both normal and lesions, in a person. Examples of CADe systems include the mammography CADe systems available commercially such as 'PowerLook Advanced Mammography Platform' from 'iCAD' and the 'ImageChecker' from 'Hologic'. The purpose of such products is to reduce the number of findings missed by a radiologist. These products attempt to achieve this by detecting suspicious regions in the image and showing these to the radiologist.

CADe systems may be used as a so-called 'Second Reader' system. This phrase is based on an approach whereby a radiologist first looks at an image resulting from a scan, for example a mammogram. The radiologist will then, based on training and experience, identify areas of the scan where the radiologist considers that there may need to be further investigation, for example a biopsy. However, the radiologist can then consider the CADe findings. Those findings might involve a display to highlight any additional suspicious regions on the mammogram. The radiologist will then, based on training and experience, look at those further areas of the scan. The CADe system is thereby, figuratively speaking, performing a second look at the scan. The results of that second look at the scan may be that the radiologist will be directed to areas of the scan that he/she had overlooked. In this way, CADe systems are designed to reduce 'false negatives', which are also termed 'missed findings'. Thus CADe systems perform a support role to clinicians.

Computer Aided Diagnosis (CADx) systems are a related technology to CADe. CADx systems attempt to solve a different problem, and relate generally to risk assessment. Instead of focussing on potentially missed findings as in CADe, they try to assist the user to classify findings correctly, either as malignant or benign in the case of cancer. They rely on the user to detect, namely identify abnormalities, but then typically provide a score indicative of risk of malignancy. There are many examples of such systems proposed within the academic literature. However, fewer systems are available commercially, and hence used in clinical practice.

This discrepancy is indicative of the difficulties in deploying practical systems with the known approaches. The output of known CADx systems is typically some kind of score. That score indicates the risk or likelihood of disease, or its absence. An example of a commercial CADx system is the 'Transpara' product from 'Screenpoint'. There are many non-clinical CADx systems in the academic literature.

In PET imaging, as used for oncological staging, i.e. determining the degree of cancer spread, the clinician is typically seeking regions of unusually high intensity that may be indicative of tumours. In this case, the clinician may make measurements of the image intensity inside a region of interest. Such measurements may include the mean, maximum or standard deviation of the intensity within a region, and correlates with the amount of radioactive tracer present in the image. In some instances, as with measurements of structural changes, it is often the change in value rather than its absolute level that is of interest to clinicians.

Size, angle and volume measurements may be made using a range of tools that are available in conventional medical imaging software. Basic systems may only provide manual tools, such as digital callipers or rulers that require the clinician to click at the ends of the object to be measured. Tools akin to protractors can be used to measure angles. More advanced systems may provide region of interest (ROI) tools that allow the user to define two-dimensional (2D) or in some cases three-dimensional (3D) regions that can be used to measure areas or volumes of regions; such regions being of a pre-specified shape, e.g. cuboid or ellipsoid or free-form such as a polygon. Yet more advanced systems allow the user to paint regions in 2D or 3D providing a greater degree of control to define regions. Such region-based tools also provide a means for the user to extract summary statistics and information from the regions, such as the mean, maximum or median of the voxels inside the region.

In addition to the above manual tools, medical imaging software may additionally provide semi-automated tools to assist the user in making measurements in an efficient and robust manner. An example of such a semi-automated tool is described in '3D General lesion segmentation in CT', by Marie-Pierre Jolly, Leo Grady and published in: '2008 5th IEEE International Symposium on Biomedical Imaging: From Nano to Macro'. This publication describes a tool that can assist the user to obtain volumetric measurements more efficiently and can help reduce the inter- and intra-user variability in measurements. However, even using such tools, the user is often left to check, and in many cases correct, the resulting segmentation in order to ensure adequate accuracy.

All the above methods are affected by the subjective judgement of the user. For the manual methods, the user must use their judgement to select the correct location to place the ends of the rulers or the points at which to define the vertices of the polygon. The document 'Intra- and Inter-observer Variability in CT Measurements in Oncology', authored by Aoife McErlean et al. and published in Radiology. November 2013, Volume 269, Issue 2, showed that the inter-reader variation for radiologists maybe between −12% and 7% for 10 mm lesions. This is likely to be sufficient to affect the subsequent management decision. Using semi-automated methods, the resulting segmentations can still be subject to variability between subsequent measurements made by the same reader and different readers. The document 'Determining the Variability of Lesion Size Measurements from CT Patient Data Sets Acquired under "No Change" Conditions 1', authored by Michael F. McNitt et al., and published in Translational Oncology. Volume 8, Issue 1, February 2015, Pages 55-64, showed that semi-automated volumetric measurements may vary up to 25%.

Fully automated methods do not suffer from user induced variability, but often fail to produce adequate segmentations and, hence, the user must correct the result thereby introducing variability and error. The issue with semi-automated and fully-automated methods is that, typically, a binary segmentation is required from with a size or volume can be extracted. Producing such a segmentation can be a difficult problem in itself and errors in the segmentation propagate to the size or volume estimate.

Furthermore, one underlying cause of such poor repeatability exhibited by known methods is that they rely on the specification of some points as a first step based upon which a size or volume can be derived. Producing such a segmentation can be a difficult problem in itself; and hence leads to errors in the segmentation propagate to the size or volume estimate.

The fundamental issue with all of the above methods is that they rely on the specification of a number of points or ROI by the user. This is a difficult problem and is generally subject to inter- and intra-user variability. The semi-automated methods may alleviate some of these problems, but still require the user to review and, if necessary, edit the proposed ROI. Since all such methods rely on correct placement of rulers, shapes or free-form regions, variations in the definition of such regions can result in large changes in the resultant quantification.

An alternative approach is to avoid the segmentation step and use a regression algorithm in order to directly estimate the size from the image. Such methods are referred to as 'segmentation-free' or 'direct' methods, Examples of segmentation-free or direct methods are proposed in the document 'Direct volume estimation without segmentation', authored by X. Zhen et al. and published in Proc. SPIE 9413, Medical Imaging 2015: Image Processing, 94132G (20 Mar. 2015). Using a direct method provides a more reliable estimate of size and volume because it bypasses the need for a binary segmentation. It generates a mapping from the image space directly to a single real number using a regression algorithm.

However, a critical limitation with such direct methods is that the user does not have a mechanism by which they can check the validity of the number. With the more conventional methods that first define a segmentation, the user can at least check that the segmentation is correct, as a means to judge the reliability of the quantification estimate. A second limitation of the direct method is that if the result is incorrect, the user has no mechanism by which to correct the output, e.g. by making adjustments.

Thus, there exists a need for an improved direct quantification technique (that encompasses volume estimation).

A yet further and important limitation of prior art direct methods is that they can only be applied to single images. The inventors of the present invention have identified and appreciated that they do not provide a measure of a change between two or more images, and only identify the measurements in each image. A simple way to estimate a change in a measurement is to use the direct measurement method, two or more times, in order to extract a measurement for each image and location; then compare the measurements over time. However, this simple approach may miss more subtle indications of change, because each measurement is necessarily only a summary of the underlying changes. For example, extracting the volume of a lesion in each image and then calculating the change in volume will miss changes in morphology that do not affect the volume, or only minimally change the volume but significantly change the shape.

In other situations, it may be difficult to define a ground-truth volume to use as training data for the direct method. For instance, defining ground-truth segmentations and volumes is inherently unreliable and subject to a great deal of inter-user and intra-user variation. This is more problematic for some anatomical structures where the ground-truth measurement is poorly defined. One example of this is for so-called Ground Glass Opacities (GGOs) and partially solid nodules that occur frequently in the lung when imaged with a Chest CT scan. Such findings are important to characterize because, whilst the vast majority are benign, a small minority will turn out to be malignant. GGOs and partially solid nodules are poorly defined objects with unclear borders. Hence, the resulting segmentations, and any measurements derived from them for use as training data, are subject to great deal of variability. Changes in the size and composition of GGOs and partially solid nodules can be an early indication of cancer. In particular, if a GGO turns into a partially solid nodule, or a partially solid nodule becomes increasingly solid, then this is highly suspicious of malignant disease. Such changes may not exhibit in changes in volume or size, only intensity pattern.

SUMMARY OF THE INVENTION

Accordingly, the invention seeks to mitigate, alleviate or eliminate one or more of the abovementioned disadvantages singly or in any combination.

According to a first aspect of the present invention, there is provided a quantification system. The quantification system includes: at least one input configured to provide at least one input medical image and provide a location of interest in the at least one input medical image; and a mapping circuit. The mapping circuit is configured to: compute a direct quantification result from the location of interest of the at least one input medical image to a quantification of interest and output a direct first quantification result therefrom; and generate a saliency map as part of the computation of the direct quantification result; and derive a segmentation from the saliency map, such that the segmentation independently generates a second quantification result that is within a result range of the direct first quantification result.

In an optional example of the invention, the mapping circuit may be at least one of: a regression circuit applying a regression algorithm, a classifier circuit applying a classification algorithm.

In an optional example of the invention, the location of interest input may include a single point or region of interest, ROI, provided by an user or an automated detection algorithm.

In an optional example of the invention, the mapping circuit may be configured to obtain an implicit segmentation using a first set of voxels of the at least one image that are identified as being more important than a second set of voxels of the at least one image in the computation.

In an optional example of the invention, the mapping circuit may be configured to map input voxels from the at least one image to a quantification of interest output value through a linear function, or series of non-linear function(s).

In an optional example of the invention, the mapping circuit may be configured to perform an additional mapping operation that modifies the saliency map such that the additional mapping function generates an implicit segmentation that is consistent with the direct first quantification result. In some examples, the additional mapping operation may employ a threshold when it independently generates the second quantification result, where the threshold may be employed if a binary segmentation is used or in an application of non-linear weighting real valued non-binary segmentation is used In an optional example of the invention, the mapping circuit may be configured to allow a user to make adjustments to the derived segmentation, such that the direct quantification result can be improved In an optional example of the invention, a regression circuit may use a Convolutional Neural Network In an optional example of the invention, a classifier circuit uses a Random Forest, or a Support Vector Machine, for classification.

In an optional example of the invention, the mapping circuit may be employed in at least one of: an interpretation of medical images in a clinical setting, for example comprising in one or more of: radiology, cardiology, oncology; a clinical trial for a medical intervention for example drug, radiation therapy.

In an optional example of the invention, the quantification system may include a part of at least one from a group of: a picture archiving communications system, an advanced visualisation software package, a modality workstation.

In an optional example of the invention, the at least one input may include a first input configured to provide at least one input medical image and a second input that provides a location of interest of the at least one input medical image.

According to a second aspect of the present invention, there is provided a method of quantifying a medical image, for example for direct volume estimation. In examples of the invention, the method includes providing at least one input medical image and a location of interest of the at least one input medical image; computing a direct quantification result from the location of interest of the at least one input medical image to a quantification of interest and output a direct first quantification result therefrom; generating a saliency map as part of the computation of the direct quantification result; and deriving a segmentation from the saliency map, such that the segmentation independently generates a second quantification result that is within a result range of the direct first quantification result.

These and other aspects of the invention will be apparent from and elucidated with reference to the embodiments described hereinafter.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

DETAILED DESCRIPTION

Examples of the invention are targeted towards medical software systems as used to support clinical decision making in healthcare environments. In particular, examples of the invention relate to a use of medical imaging by medical professionals in order to manage patients and screening subjects. It is envisaged that examples of the invention may be applied to patients undergoing imaging investigation for the presence or absence of disease, response to therapy, post-therapy monitoring or as part of a screening programme.

As mentioned, known direct volume estimation techniques suffer from the fact that an user does not have the means (hardware or software or firmware) by which they can check a validity of the direct volume output estimated number, and, if the result is incorrect, the user has no means (hardware or software or firmware) by which to correct the output by making adjustments. Examples of the present invention address these two fundamental limitations in a new direct volume estimation approach, such that the user has a means to assess the accuracy of the direct quantification and adjust it, if necessary.

In some aspects of the invention, the limitations of known direct quantification methods are overcome by deriving a segmentation from the direct quantification result and displaying this to the user, such that the user can check whether the presented quantification is accurate and reliable. In a second aspect of the invention, the user is then allowed to make adjustments to the derived segmentation, such that the result can be improved.

Figure 1:
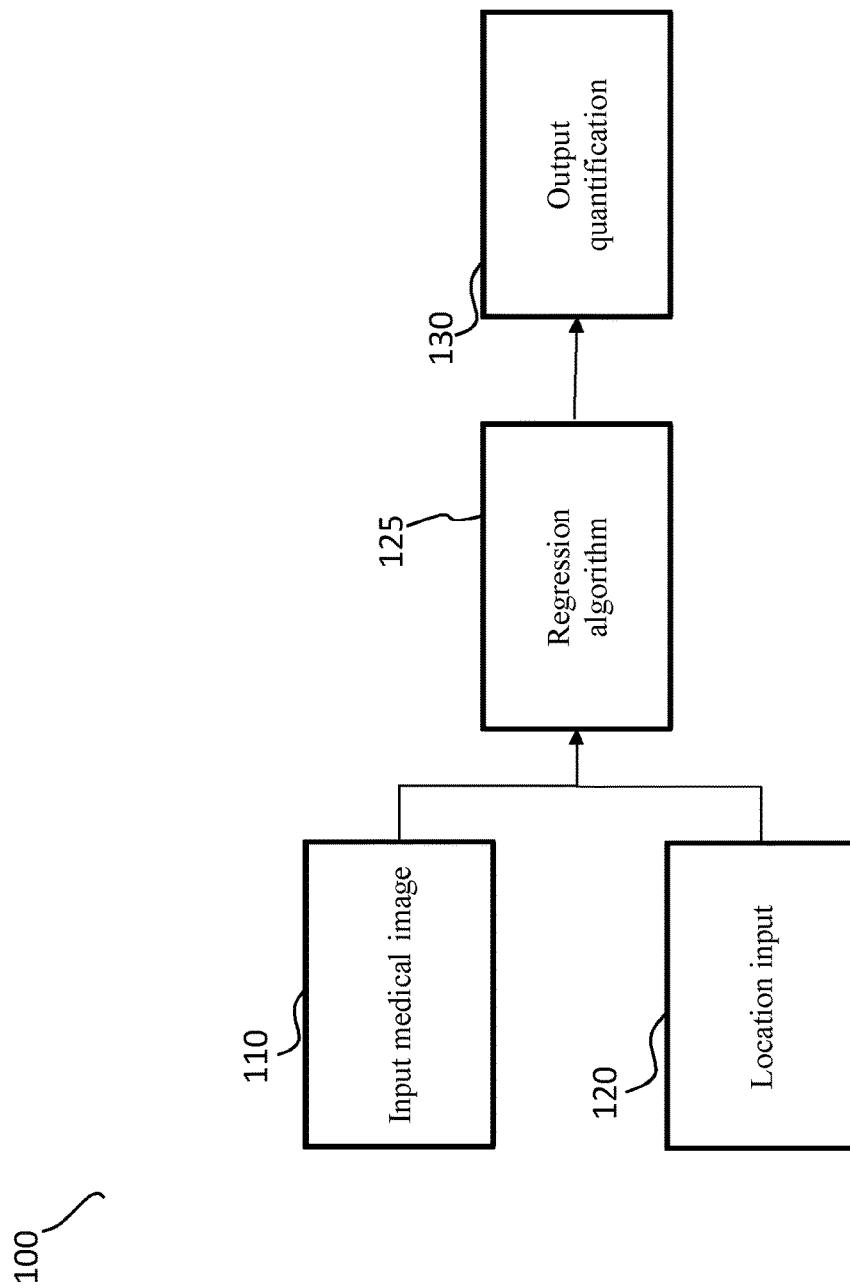
FIG. 1 illustrates an example block diagram of a direct quantification system, according to examples of the present invention.

Referring now to FIG. 1, an example block diagram illustrates an overview of a direct quantification system 100, according to examples of the present invention. The inputs to the system are a medical image 110, for example either 2D, 3D or 4D (e.g. 3D medical image acquired over time) and a location of interest input 120. The location of interest input 120 can be specified in a number of ways, but typically could be a single point or region of interest (ROI) provided by the user or an automated detection algorithm. The ROI is used to provide the system an approximate area of the image that is of interest to the user, but will not provide a detailed segmentation of the anatomical object of interest. For example, it could be a cuboid around a lesion. A mapping circuit, which in this example is a regression circuit applying a regression algorithm 125, maps the voxels from the image to the quantification of interest, referred to herein as the 'Output Quantification' 130. For example, the direct quantification system 100 may map the intensity values within the cuboid to a single real number that measures a lesion's size. In some examples, the direct quantification system 100 may output several such quantifications. In some examples, the direct quantification system 100 may output vectors rather than scalars.

In some examples, the regression algorithm 125 may be implemented using one of a number of methods known in the art, including Support Vector Regression, Random Forest Regression or Convolutional Neural Networks (CNNs). Such methods should first be trained using a corpus of training where the input and desired or ground-truth output values are known, as illustrated with respect to the example of FIG. 2. In the following example embodiments, we shall assume a CNN-based implementation. However, it is envisaged that other techniques can be used and are contemplated as being encompassed in the concepts herein described.

Moreover, in some examples, it is envisaged that the mapping circuit, which in this example is a regression circuit applying a regression algorithm 125, may be replaced with a mapping circuit, which is a classifier circuit that applies a multi-way classification algorithm. In regression, the system has one or more outputs that are the output measurements. In an example implementation of the invention that uses multi-way classification, the direct quantification system 100 may be configured to output one of a number of output indicators, each output indicator representing a range of values of the output measurement. For example, if the output measurement spans scalar values from '0' to '100', then a multi-way classifier providing '10' outputs may be utilized. For some applications of the mapping circuit, multi-way classifiers may provide a more convenient approach than direct regression methods.

Figure 2:
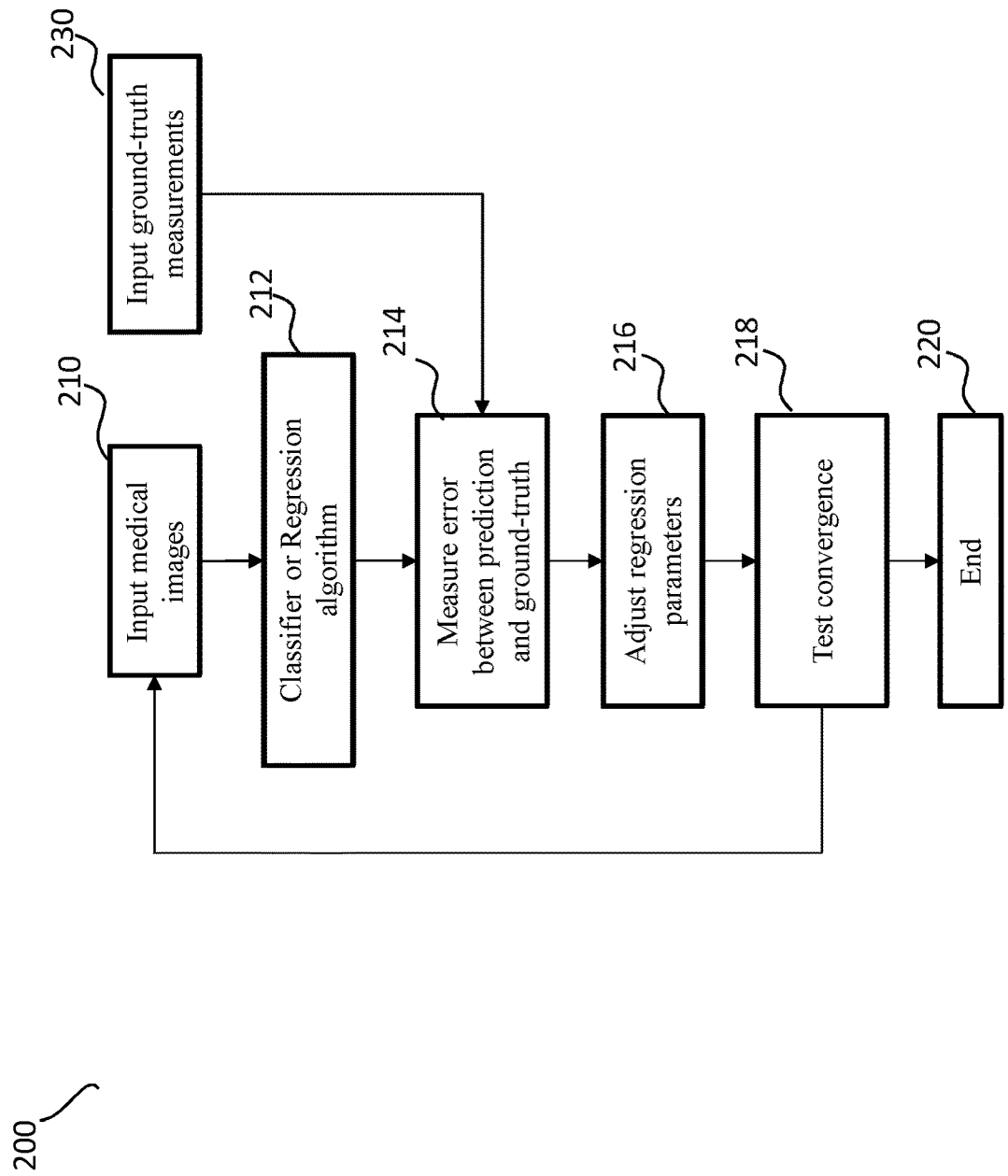
FIG. 2 illustrates an example flowchart of an approach to train a mapping circuit, which in this example is a regression circuit applying a regression algorithm in a direct quantification system, according to examples of the present invention.

FIG. 2 illustrates an example flowchart 200 of an approach to train a mapping circuit, which in this example is a regression circuit applying a regression algorithm employed in a direct quantification system, such as regression algorithm 125 of FIG. 1, according to examples of the present invention. Regression algorithms are trained using specific methods designed for that particular regression technique. The flowchart 200 of FIG. 2 shows a generic high-level overview of how training may be performed in accordance with examples of the invention. The input to training is typically a set of medical images at 210, each medical image associated with a ground-truth measurement 230. A regression algorithm (or in other examples a classification algorithm) is initiated at 212 and an error measured at 214 between the predicted direct quantification measurement and the input ground truth measurements 230.

In some examples, the training iterates over all the set of training images and measures the degree to which the regression algorithm correctly predicts the desired output. In this example, the parameters of the regression algorithm are adjusted at 216, so as to iteratively reduce the training error measured at 214, that is, the difference between the correct output and the one predicted by the regression algorithm at each iteration of training. Once the parameters and/or the training error do(es) not reduce further, and convergence has been achieved at 218, training stops at 220.

Implicit Segmentation

In order to address the first shortcoming of the known direct quantification measurement approach, examples of the invention note that each measurement produced by the system implies a certain segmentation. This is because the direct quantification assessment process, for example using a mapping circuit, which in this example is a regression circuit applying a regression algorithm, is configured to map the input voxels to an output value through a linear, or more typically a series of non-linear, function(s). Examples of the invention utilise the fact that certain voxels have a greater impact on the output measurement than others. Hence, in some examples, the voxels that count most to the output measurements are identified and shown to the user, so that the user can use these more important and relevant voxels to assess whether (or not) the output is accurate or reliable.

In effect, examples of the invention reverse the conventional approach of first obtaining a segmentation and then extracting quantifications. Here, examples of the invention adopt the approach to first obtain an output quantification directly from the image, and then obtain the implicit segmentation using the voxels that are most important in the measurement.

Figure 3:
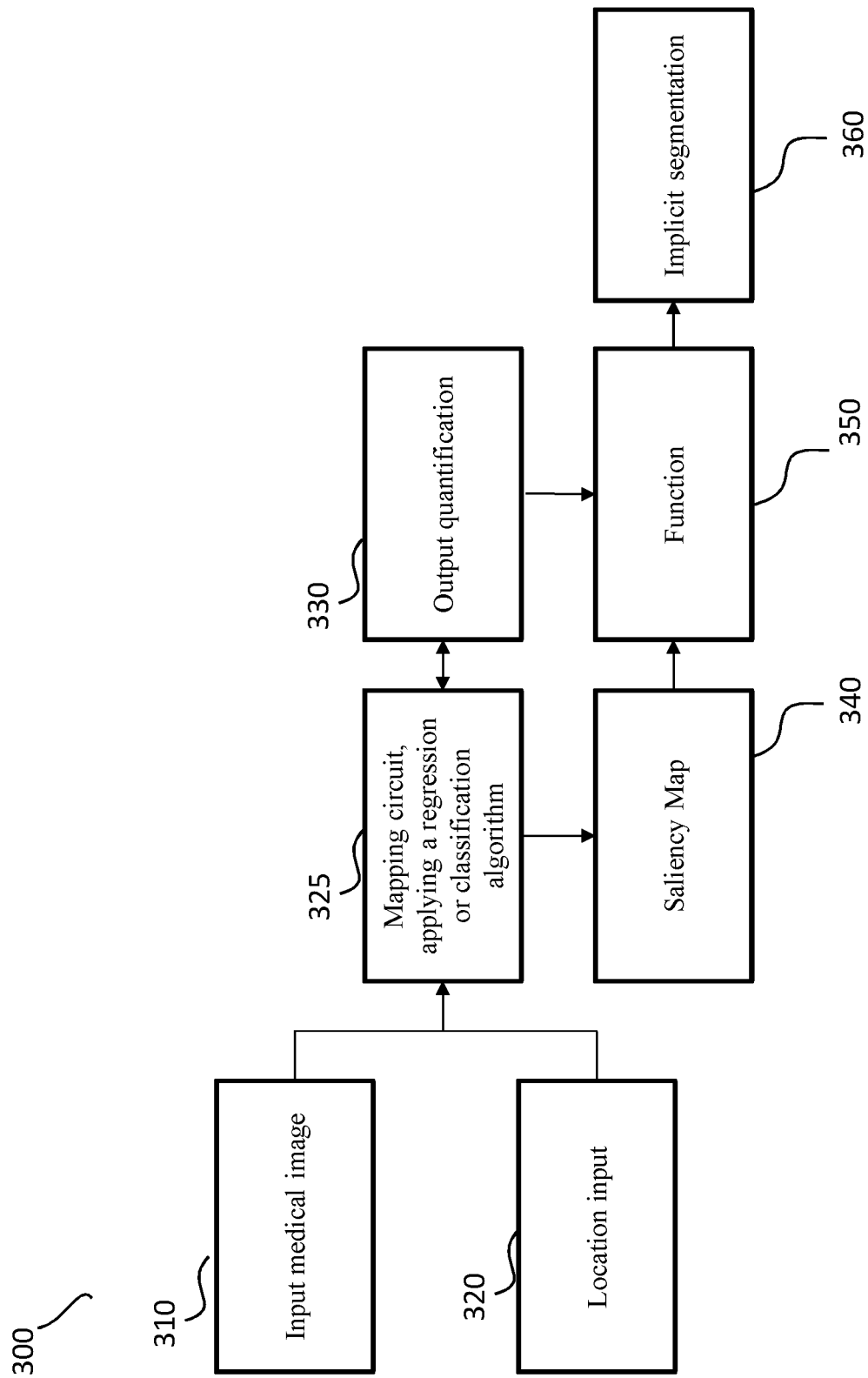
FIG. 3 illustrates an example block diagram showing how the implicit segmentation is generated, according to examples of the present invention.

Referring now to FIG. 3, an example block diagram 300 illustrates how the implicit segmentation may be generated, according to examples of the present invention. In examples of the invention, it is envisaged that the output quantification data may be generated in a substantially simultaneous manner to a saliency map. In other examples, it is envisaged that the saliency map may be generated after the generation of the output quantification data. It is envisaged in some examples of the invention that it may be more convenient to produce both the measurement and the implicit segmentation simultaneously, rather than sequentially.

The inputs to the direct quantification system are a medical image 310, for example either 2D, 3D or 4D (e.g. 3D medical image acquired over time), a location of interest input 320 and notably the Output Quantification 330. The location of interest input 320 may again be specified in a number of ways, but typically may be a single point or region of interest (ROI) provided by the user or an automated detection algorithm.

In this example, an implicit segmentation is extracted from the mapping circuit 325, which in this example is a regression circuit applying a regression algorithm (or alternatively the mapping circuit 325 may use a classifier circuit applying a classification algorithm in other examples). For example, the specific details of how to obtain an implicit segmentation from the regression algorithm may depend on the implementation of the regression algorithm. Assuming a CNN implementation there are several methods envisaged in example embodiments that may be employed to extract what are known as activation or saliency maps 340 from a trained CNN. Such maps 340 have been used in object classification literature that may be adapted for use in examples of the invention, such as described in 'Deep inside convolutional networks: Visualising image classification models and saliency maps', authored by Simonyan et al., and published in the Workshop at International Conference on Learning Representations (2014), which is incorporated herein in its entirety.

Such object classification methods are intended to produce activation or saliency maps that indicate where an object is present in the image. However, they cannot be used directly to produce an accurate segmentation that relates to the quantification, because the maps 340 show the relative importance of voxels to the output of the regression or classification. In order to be used by a user, examples of the direct quantification system 300 require an absolute or calibrated output that is consistent with the estimate measurement.

Thus, examples of the invention introduce an additional mapping function 350 that is applied to a saliency map 340 generated from an output of the mapping circuit 325, which in this example is a regression circuit applying a regression algorithm (or may use a classifier circuit applying a classification algorithm), in order to produce an implicit segmentation 360 that is consistent with the current measurement, i.e. a segmentation that can be used directly to produce the output quantification that has been estimated by the mapping circuit 325. In some examples, this additional mapping function 350 may be a threshold, if a binary segmentation is required. Alternatively, in some examples, this additional mapping function 350 may be an application of non-linear weighting, where a soft, i.e. real valued non-binary, segmentation is desired. In either case, examples of the invention define the additional mapping function 350 such that the resultant segmentation can be used, along with the input medical image 310, to produce the same output quantification as produced by the mapping circuit 325.

Figure 4:
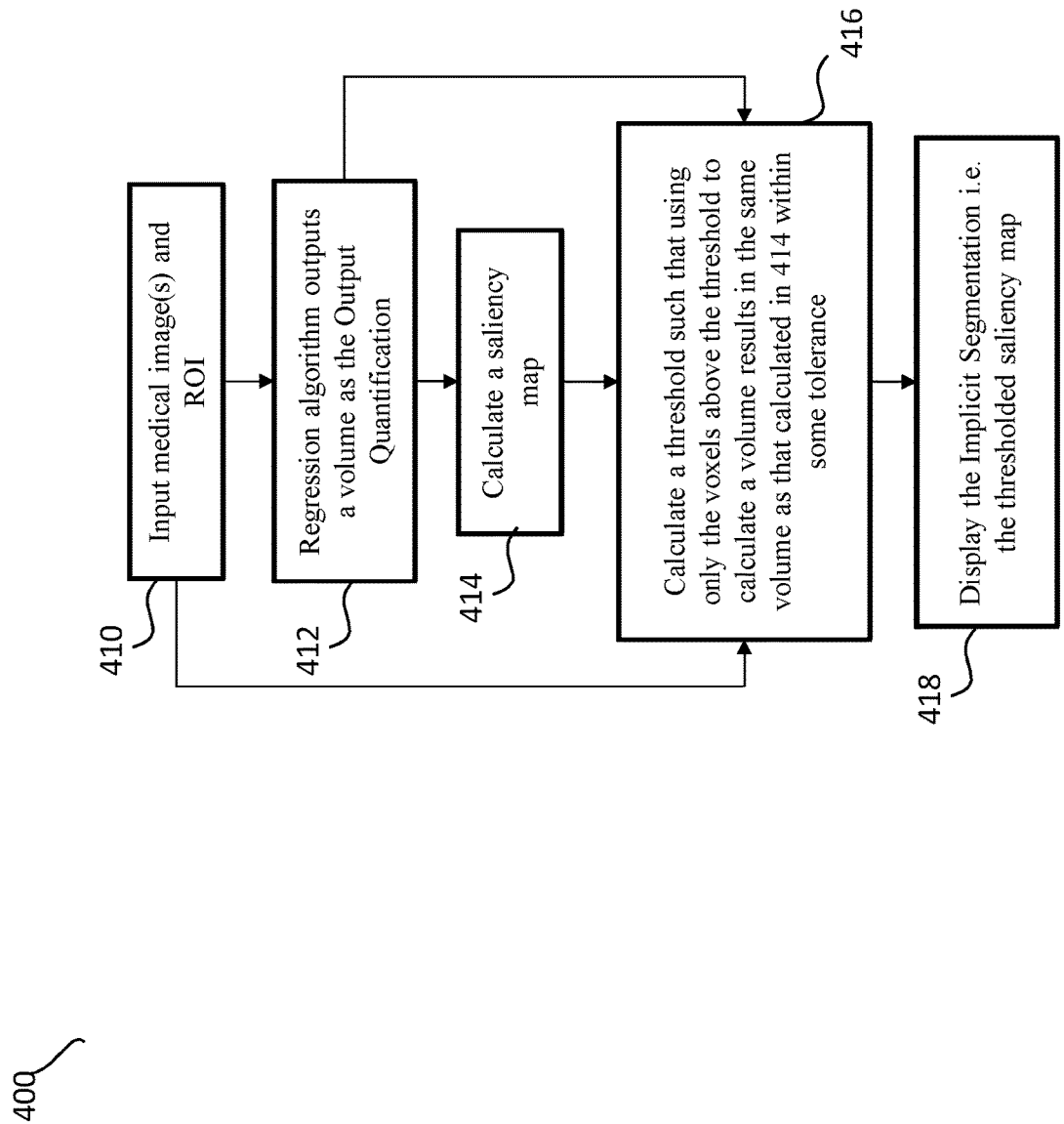
FIG. 4 illustrates an example flowchart showing one approach detailing how the implicit segmentation may be obtained from the saliency map, according to examples of the present invention.

Referring now to FIG. 4, an example flowchart 400 illustrates one approach on how the implicit segmentation may be obtained from the saliency map, according to some examples of the present invention. At 410, the method first maps input medical image(s) and the location input, such as an ROI input, which in this example is a regression circuit that regresses the output volume directly from the input medical image(s) and the location input. Here, in this example, the mapping function is a threshold and the output quantification is a volume, as shown at 412. Next, at 414, the saliency map is created using the output volume, the input images and the location input, such as ROI. Each voxel in this saliency map encodes the relative importance of each voxel to the final measurement. Next, at 416, a threshold is determined such that, if only those voxels that exceed the threshold are counted in a volume estimation, then the resultant volume is exactly the same or very close (within, say, a pre-defined threshold) to the estimated volume from 410. Thus, in this manner, the second quantification result (e.g. the volume estimation) is within a result range (i.e. substantially the same result or within the pre-defined threshold value) of the direct first quantification result from 410. The implicit segmentation is then the result of the threshold applied to the saliency map. This is shown to the user at 418 to assess the reliability of the measurement. Thus, in some examples, the segmentation from the saliency map is such that the segmentation independently generates a second quantification result that is within a result range of the direct first quantification result.

In some examples, the implicit segmentation may be a binary mask indicating those voxels that are the most important in obtaining the segmentation. Alternatively, it may be a soft-output segmentation where each voxel is given a weight according to its relative importance to the Output Quantification.

Some examples of the invention have been described with reference to the direct quantification system first producing a measurement and thereafter the implicit segmentation. However, it is envisaged that in other examples of the invention, it may be more convenient to produce both the measurement and the implicit segmentation simultaneously, rather than sequentially.

Correction of Errors

A further aspect of the invention is to provide a mechanism by which the measurement, which is/may be produced by the direct quantification system herein described, can be adjusted if the user deems that there are errors in the implicit segmentation, and hence the measurement. Two possible implementations of such user adjustment of the output (e.g. correction of error(s)) are given by way of example.

Figure 5:
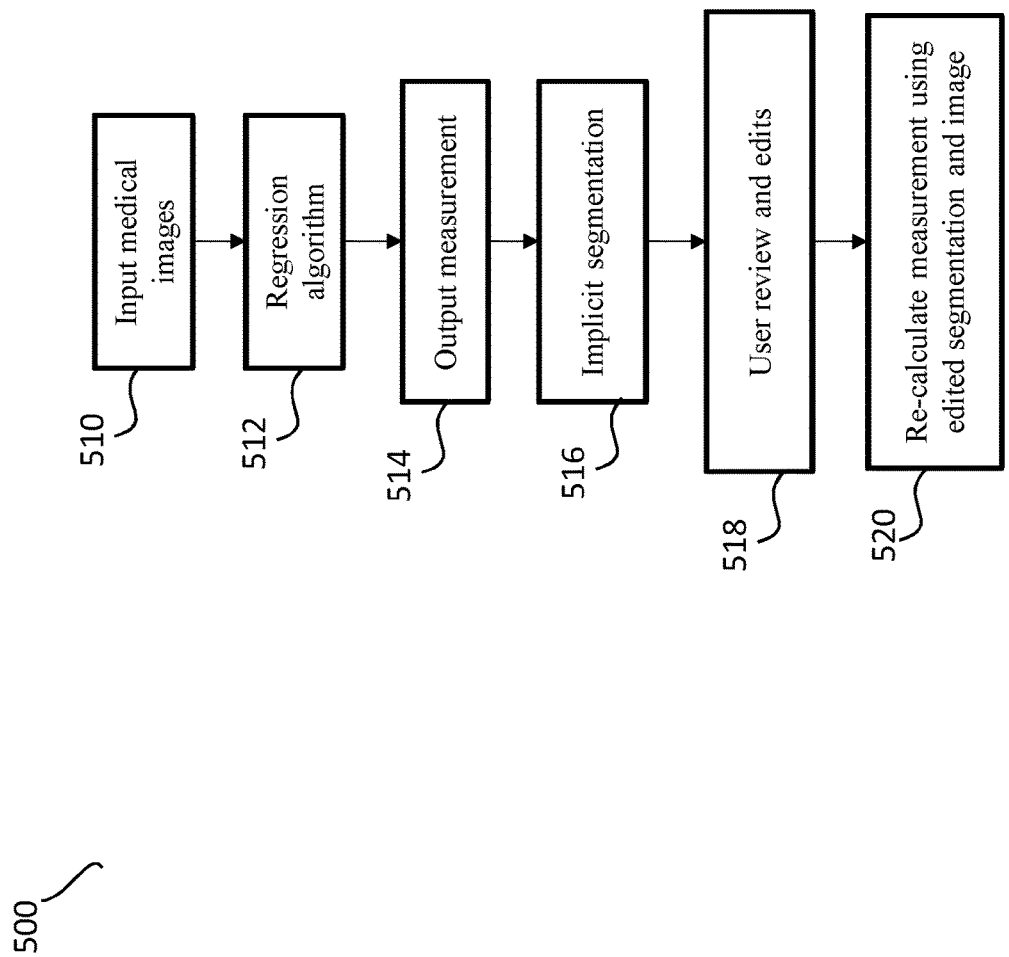
FIG. 5 illustrates a first example flowchart implementation detailing how a user may edit the implicit segmentation to update/correct the measurement, according to examples of the present invention.

Referring first to FIG. 5, a first example flowchart 500 implementation illustrates how a user may edit the implicit segmentation to update/correct the measurement, according to some examples of the present invention. Here, one or more medical images are input to the direct quantification system at 510 and a mapping circuit, which in this example is a regression circuit applying a regression algorithm, is run at 512. At 514 the direct quantification system first calculates the output quantification, then derives an implicit segmentation at 516 for the measurement. This is displayed to the user for checking at 518. If the user deems that the output quantification and segmentation are inaccurate, then the user may edit the segmentation directly using, say, interactive paint and edit tools to adjust the segmentation directly.

In some examples, if the segmentation is a binary mask, then the user may be allowed to adjust which voxels are included, and which excluded, from the calculation of the output segmentation. If the implicit segmentation is a soft segmentation, then the user has more control to adjust the importance of voxels that count towards the output quantification. At 520, once the user has adjusted the segmentation, then the direct quantification system recalculates the quantification using the image and the segmentation in the conventional way.

Figure 6:
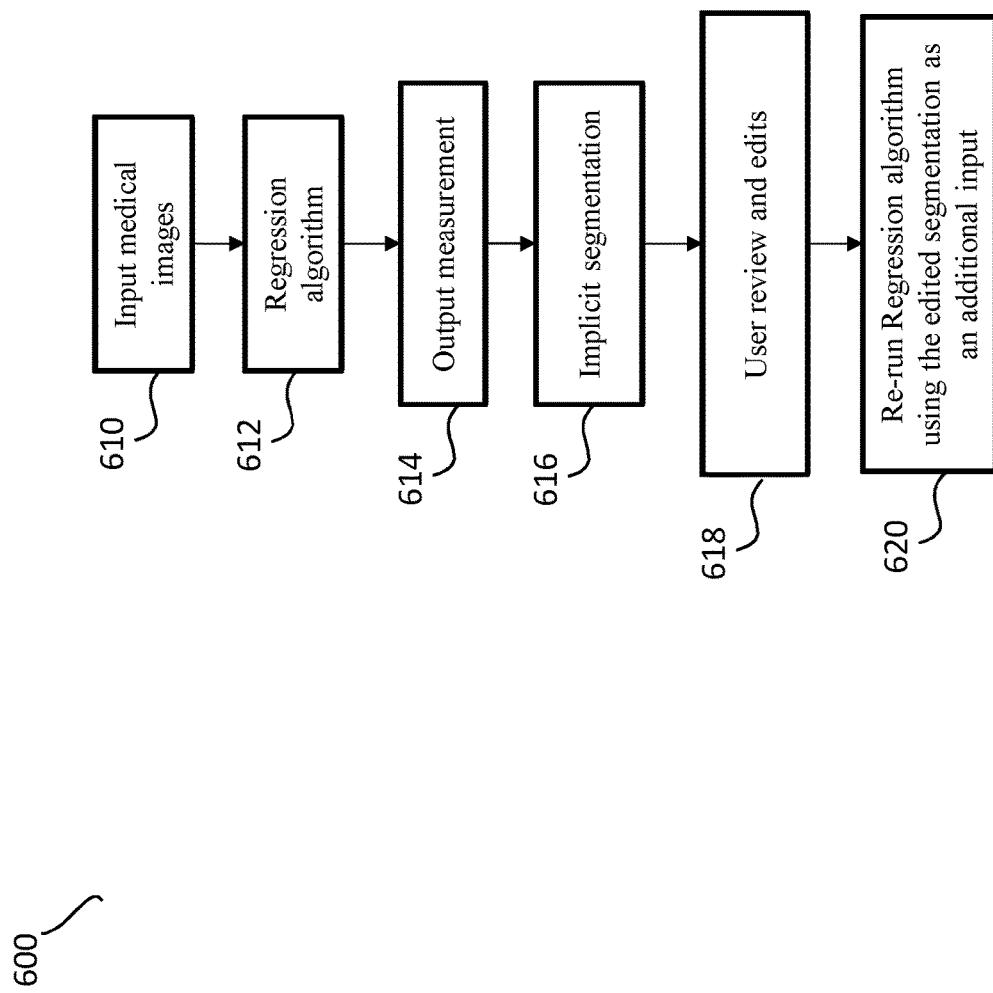
FIG. 6 illustrates a second example flowchart implementation illustrating how user edits to the implicit segmentation may be used to update/correct the measurement, where the updated segmentation is used as an input to the mapping circuit, which in this example is a regression circuit applying a regression algorithm, according to examples of the present invention.

Referring now to FIG. 6, a second example flowchart 600 illustrates how a user may edit the implicit segmentation to update/correct the measurement, where the updated segmentation is used as an input to mapping circuit, which in this example is a regression circuit applying a regression algorithm, according to examples of the present invention. Here, again, one or more medical images is/are input to the direct quantification system at 610 and a regression algorithm is run at 612. At 614 the direct quantification system first calculates the output quantification, then derives an implicit segmentation at 616 for the measurement. This is displayed to the user for checking at 618. If the user deems that the output quantification and segmentation are inaccurate, then the user may edit the segmentation directly using, say, interactive paint and edit tools to adjust the segmentation directly.

In some examples, if the segmentation is a binary mask, then the user may be allowed to adjust those voxels that are included and those voxels that are excluded from the calculation of the output segmentation. If the implicit segmentation is a soft segmentation then the user has more control to adjust the importance of voxels that count towards the output quantification.

In this second example, at 620, once the user has adjusted the segmentation, then the direct quantification system is able to re-calculate the quantification using the image and the edited segmentation. Here the adjusted segmentation may be used to weight the input image, such that the regression algorithm takes into account the user's adjustments to alter the measurement. If the segmentation is binary, then the user adjustments are binary values indicating to the regression algorithm which voxels sounds be considered in the measurement and which should be excluded. For soft segmentations, the user's edits are used to indicate to the regression algorithm the relative importance of each voxel for the measurement. In some examples, the regression algorithm should have been previously developed and trained, such that it can optionally take a segmentation as an additional input. In some examples, when used for the first time, where no user edits have been made, the segmentation can weight all the voxels equally.

In this manner, examples of the invention have proposed a direct quantification system and method that are able to derive an implicit segmentation from the output quantification that corresponds to the measurement. In some examples, this may allow the user to update the segmentation and/or update the measurement.

In some examples, a mapping circuit in a form of a regression circuit applying regression algorithms may be employed. In some alternative examples, a mapping circuit in a form of a classifier circuit applying a multi-way classification may be employed. In some examples, CNNs may be employed that provide state of the art results and are a convenient way to implement the inventive concepts herein described.

Thus, examples of the invention propose a direct quantification technique that performs a direct quantification assessment of at least one input medical image and a location of interest input to produce a direct quantification result, and derive a segmentation from a saliency map as part of the computation of the direct quantification result, such that the segmentation produces a quantification result that has the same value as the direct quantification result, but derived in an independent manner.

This segmentation computed data (that can support the independent verification of the direct quantification result via means independent to the direct quantification result) may then be of use to a clinician (e.g. a user) when displayed to the user such that the user is able to determine whether the presented quantification is accurate and reliable.

In some examples, the segmentation derivation may include obtaining an implicit segmentation using voxels that are identified as being most important in the measurement.

In particular, some examples of the invention may further allow the user to make adjustments to the derived segmentation, such that the direct quantification result can be improved.

In particular, some examples of the invention describe a direct quantification assessment that uses a mapping circuit applying at least one of: a regression circuit applying a regression algorithm, a classifier circuit applying a multi-way classification algorithm.

Some examples of the invention also support a location of interest input to be taken into account by the direct quantification assessment, which may be specified in a number of ways, but may include a single point or region of interest (ROI) provided by the user or an automated detection algorithm. When ROI is employed, an approximate area of the image that is of interest to the user is provided to the system but this will not be a detailed segmentation of the anatomical object of interest.

In some examples, the mapping circuit, which in this example is a regression circuit applying a regression algorithm, may be configured to map the input voxels from the image to the quantification of interest, i.e. to an output value through a linear, or more typically a series of non-linear, function(s). In some examples, embodiments focus on certain voxels that have a greater impact on the output measurement than others, which are then showed to the user to assess whether (or not) the output is accurate or reliable.

In some examples, an additional mapping function may be introduced to modify a saliency map generated from an output of the regression algorithm in order to produce an implicit segmentation that is consistent with the current measurement. In some examples, the additional mapping function may be a threshold, if a binary segmentation is required or an application of non-linear weighting, where a soft, i.e. real valued non-binary, segmentation is desired.

Although examples of the invention have been described with reference to the direct quantification system using a Convolutional Neural Network for the regression algorithm, it is envisaged that the concepts described herein may be used with Random Forest, or a Support Vector Machine for classification.

Although examples of the invention have been described with reference to an interpretation of medical images in a clinical setting e.g. in radiology, cardiology, oncology, it is envisaged that in other examples, the concepts described herein may be employed, say, within a clinical trial for a medical intervention e.g. drug, radiation therapy, etc.

Further aspects of the invention also address the limitation that direct methods can only be applied to single images by providing a means by which changes can be measured from a pair or more of images (or image regions) directly, whilst providing means for training the system even when ground-truth measurements are not available. This change can be measured as an absolute change, a relative change or can be normalised by the amount of time between the pair or more of images (or image regions), as each image typically has a time tag that defines when it was acquired (for example in the amount of months between the respective images).

Some examples of the invention overcome the limitation of the prior art by providing means by which two, or more images, and information corresponding to particular locations within the images, can be used to produce measurements of change directly without the need for segmentation and without the need to extract measurements from each image.

Some examples of the invention overcome the need to provide ground-truth measurements of change by providing means by which the system can be trained using ordered pairs or ordered multiples of training data. Ground-truth is an accepted reference, typically validated by a clinician, e.g. a clinician saying that an image has or has not changed, against which we train. Hence, a ground-truth output could be binary, i.e. an image has or has not changed. Alternatively, the ground-truth could have intermediate levels, in the context of ordered pairs, such as not changed, changed a little or changed a lot.

In some examples of the invention, a system and method are described by which the system can provide measurements of change that correspond to the state of the patient or state of the disease when it has been trained using ordered pairs or multiples of training data.

In some examples of the invention, a system and method are described by which the system can provide changes in the images that are artefacts of the imaging process and do not correspond to the real changes in the state of the disease are ignored.

In some examples of the invention, a system and method are described by which the measurements of change are robust to misalignments between the image locations provided as input.

Figure 7:
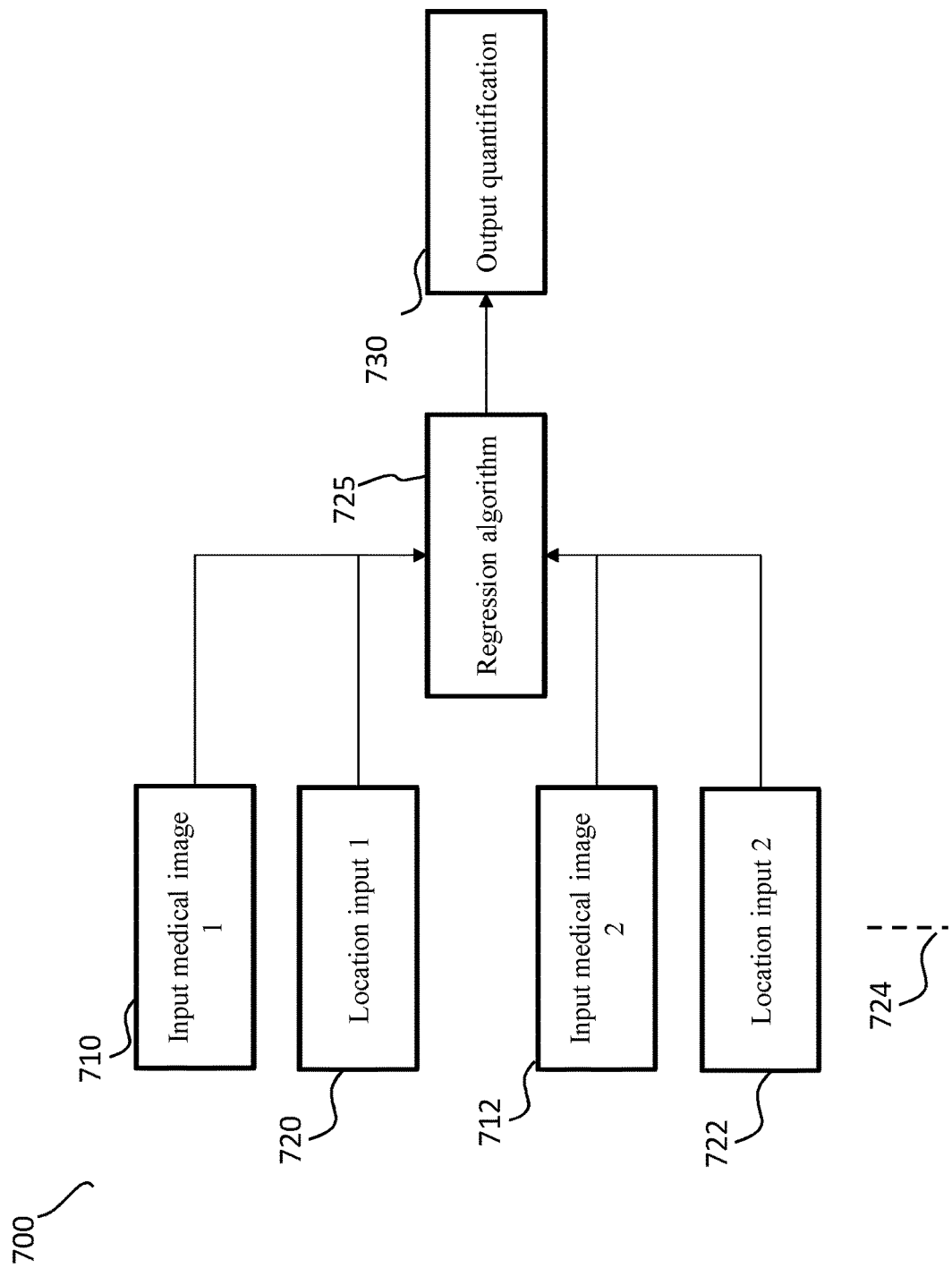
FIG. 7 illustrates a further example block diagram of a direct quantification system using a direct quantification of changes in a machine learned regression algorithm, according to examples of a further aspect of the present invention.

Referring now to FIG. 7, a further example block diagram illustrates an overview of a direct quantification system 700, using a direct quantification of changes in a machine learned regression algorithm, according to examples of the further aspect of the present invention. In this example, there are multiple inputs to the system, including a first input 710 of a first medical image and a second input 712 of a second medical image, for example either 2D, 3D or 4D (e.g. 3D medical image acquired over time). Furthermore, in this example, the multiple inputs to the system include two locations of interest at third input 720, and fourth input 722. The two locations of interest should approximately correspond to the same anatomical region. In this particular example two images are used, however the direct quantification system 700 may be readily extended to measure change over more images and more locations 724, or indeed differences between different regions in the same image for example comparing left and right regions of the body that should exhibit symmetric values. Thus, in some alternative examples, it is envisaged that different numbers of medical images and locations of interest may be input, e.g. one medical image with two locations of interest. It is envisaged that examples of the invention may also be used to compare regions between different patients, so as to estimate the changes in a cohort of different patients in a population. Although FIG. 7 shows four (or more) inputs 710, 712, 720, 722, 724 providing medical images and locations of interest, it is envisaged that in some examples of the invention, fewer inputs may be used. For example, it is envisaged that one input may be used to provide all medical images and locations of interest. Alternatively, in some examples, it is envisaged that, say, two inputs may be used, with one providing medical images and one providing locations of interest, say.

In this example, each 'location' can be specified in a number of ways, but typically could be a single point or region of interest (ROI) provided by, say, the user or an automated detection algorithm. The ROI is used to provide the system an approximate area or part of the image that is of interest to the user but will not provide a detailed segmentation of the anatomical object of interest. Again, for example, it could be a cuboid around a lesion. The mapping circuit, which in this example is a regression circuit applying a regression algorithm 725, maps the voxels from the image to the quantification of interest—referred in this document as the Output Quantification 730. For example, the direct quantification system 700 may map the intensity values within the cuboid to a single real number measuring a lesion's size. In some examples, the direct quantification system 700 may output several such quantifications. In other examples, the direct quantification system 700 may output vectors rather than scalars.

In some examples, the regression algorithm 725 may be implemented using one of a number of methods known in the art, including Support Vector Regression, Random Forest Regression or Convolutional Neural Networks (CNNs). Such methods must first be trained using a corpus of training data where the input and desired or ground-truth output values are known, as illustrated with respect to the example of FIG. 8. In the following example embodiments, we shall assume a CNN based implementation, but it is envisaged that other techniques can be used and are contemplated as being encompassed in the concepts herein described.

Moreover, in some examples, it is envisaged that a mapping circuit in a form of a regression circuit applying a regression algorithm 725 may be replaced with a multi-way classifier circuit applying a classification algorithm. In regression, the system has one or more outputs that are the output measurements. In contrast, in an example implementation of the invention that uses multi-way classification, the direct quantification system 700 may be configured to output one of a number of output indicators, each one representing a range of values of the output measurement. For example, if the output measurement spans scalar values from '0' to '100', then a multi-way classifier providing '10' outputs may be utilized. For some applications, multi-way classifiers may provide a more convenient and/or easier approach to implement than direct regression methods.

Figure 8:
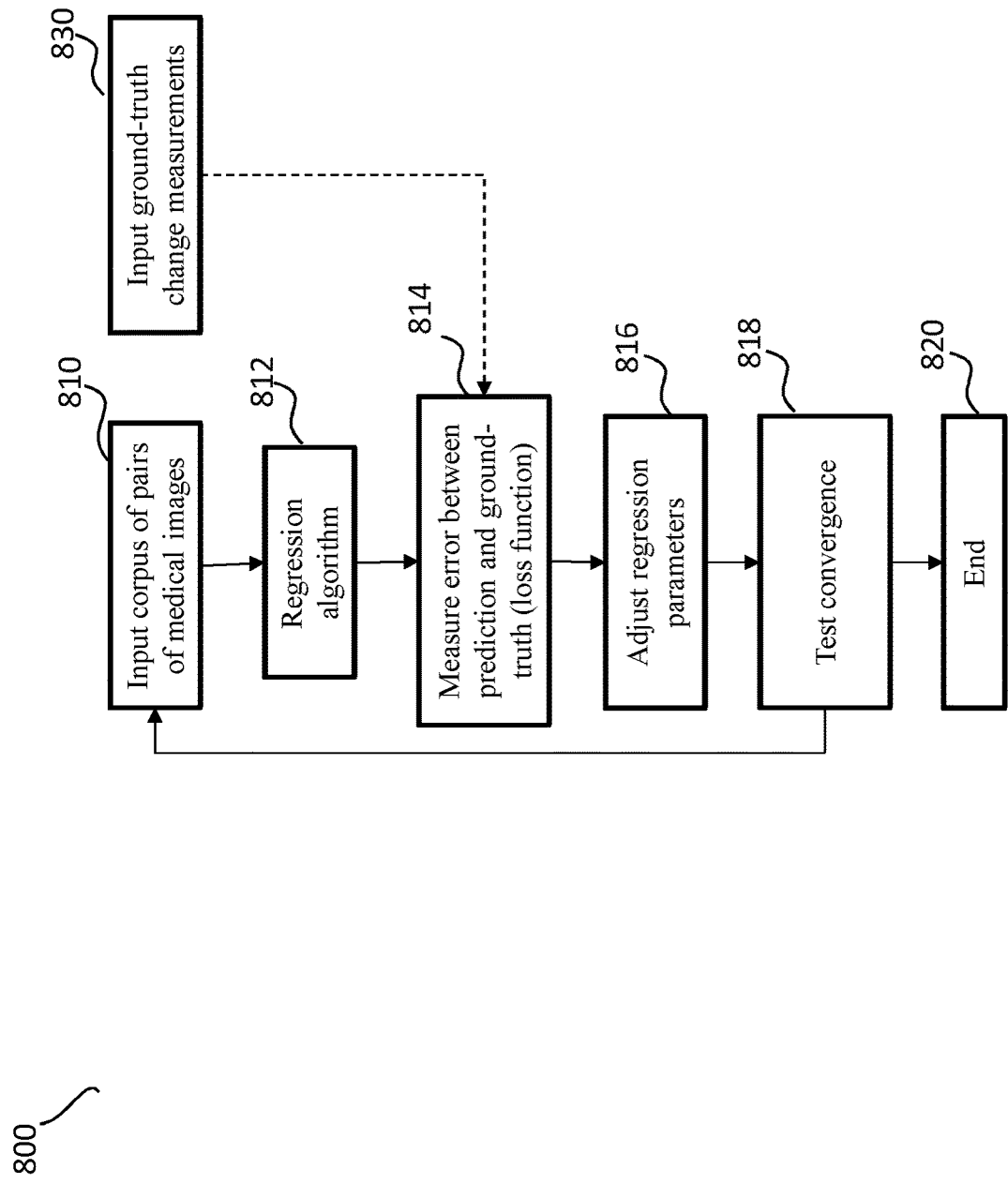
FIG. 8 illustrates an example flowchart of an approach to train a mapping circuit, which in this example is a regression circuit applying a regression algorithm in a direct quantification system, according to examples of the further aspect of the present invention.

Referring now to FIG. 8 an example flowchart 800 illustrates an approach to train a mapping circuit, which in this example is a regression circuit applying a regression algorithm employed in a direct quantification system, such as regression algorithm 725 of FIG. 7, according to examples of the further aspect of the present invention. Regression algorithms are trained using specific methods designed for each regression technique. The flowchart 800 of FIG. 8 shows a generic high-level overview of how training may be performed in accordance with examples of the invention. In some examples, the input to training may be a corpus of pairs of medical images at 810, each associated with a ground-truth change measurement 830. Ground-truth measurement changes need to be accurate and robust for the training to converge to a good solution that produces accurate results. Where possible, these should be obtained from well curated and accurate measurements that are checked for accuracy. Preferably, multiple estimates of the ground-truth should be obtained, with the consensus used for training. A mapping circuit, which in this example is a regression circuit applying a regression algorithm, is initiated at 812 and an error measured at 814 between the predicted measurement and the input ground truth change measurements 830.

The training iterates over all the training images and measures the degree to which the regression algorithm correctly predicts the desired output. In this example, the parameters of the regression algorithm are adjusted at 816 so as to iteratively reduce the training error measured at 814, that is, the difference between the correct output and the one predicted by the regression algorithm at each iteration of training. Once the parameters and/or the training error does not reduce further, and convergence has been achieved at 818, training stops at 820.

Training in the Absence of Ground-Truth Change Measurements

In some cases, the inventors haves identified that obtaining reliable measurements of change, to use as training data, is difficult or at least the data may be unreliable. For example, some anatomical structures are difficult to define and segment accurately and consistently. In other cases, the changes may be only qualitatively assessed and training samples only ordered in some form of ranking. For example, in the example of GGO nodules in Chest CT, their progression to partial solidity and then solid nodules cannot easily be quantified in a meaningful way, but they can be readily ordered by a human. In yet other situations, it may be prohibitively expensive or impractical to quantify each example accurately. For example, manual segmentation of cortical thickness is a time-consuming process and, hence, may not be feasible for some or all of the training data.

Therefore, in one variation of the system examples of the invention provide a mechanism by which the system can be trained using training data that has been ranked but where no quantitative measures have been made. To illustrate this approach, let us consider an example where the system needs to quantify changes in GGOs over a pair of images taken over time. First, the training data should be ranked. To do this, each pair of images is shown to a user with information regarding the date and time at which they were acquired. The user can then specify whether they consider the images as unchanged or whether the image acquired later has grown or shrunk with respect to the first image. This process can proceed over all pairs of images in the training set and using multiple users, preferably experts, to rank the images.

Next, the system must be trained. This can proceed as described earlier and as illustrated in FIG. 8, except that the loss function in 814 is changed so that it measures whether the regression algorithm in 812 has correctly ranked the pair of images during training. In the previous approach, since the ground-truth data is available then, the loss function measured the error in predicting that the pairs of images had been correctly ranked.

In some cases, it may be beneficial to provide partial ground-truth measurements to the training data. For example, in the example discussed above of cortical thickness some of the training data examples can have exact quantifications and, hence, measurements of change, whereas others can be ranked. Some examples of the invention can be adapted to handle this situation also by changing the loss function, such that where change measurements are available with particular examples in the training data, then the loss function calculates an error based on that; and where only ranks are available then it uses a loss based on that only. This approach has the advantage that the system will tend to learn change measurements that relate to the ground-truth provided, even though it was only provided for part of the training data. In contrast providing only ranks will result in predicted change measurements that do not relate to particular units or to a particular scale. In contrast, they will just reflect the degree of change across a corpus of training data.

In other examples, it is envisaged that the ranking or ordering of the training data may take many forms and may use triplets or other multiples for producing the ranking.

Relating Ranking to Changes in Clinical Condition

Where the training data also comes with some labels relating to the patient's underlying state of disease, then this too can be incorporated in some of examples of the training process. For example, in the GGO application discussed above, it is envisaged that, for each patient and GGO/nodule, a determination may result in an ultimate diagnosis of the patient as having developed cancer (or not). Therefore, where only nodule ranking has been provided, as described in the previous section, it is envisaged that examples may also adapt the loss function such that any loss relating to malignant pairs of nodules is given a greater loss or is to be predicted to greater values in the measurement than those that are ultimately found to be benign. In this manner the direct quantification system 700 may be able to learn to provide measurements of change that relate to the change in a disease state in the patient. It is envisaged that this approach may also be used to incorporate risk of disease in learning the measurement of change, e.g. patients with a greater risk of disease may be given greater values than those with lower risk.

NO CHANGE TRAINING EXAMPLES

There are examples where changes that are apparent in training inputs are artefacts of the input data and may not be reflective of a real change in the patient. For example, repeated imaging of a lesion in a body, in quick succession, will show small changes in the lesion appearance simply due to changes in a patient's position, e.g. due to breathing, or imaging artefacts. It is for this reason that many guidelines for assessing change quantitatively suggest a use of generous thresholds. For example, a greater than 20% change in volume in a lesion should be measured before considering it a true change in the state of the disease. Numerous so-called 'coffee-break' studies have been performed where a patient is repeatedly imaged with a gap of only a few minutes (hence the name) to assess such artefacts.

Using such data where it is known that the changes are not real but are artefacts in the data can be useful for calibrating the change measurement system, in order to produce low or zero change measurements under such examples.

It is envisaged that such examples can be incorporated into the training data as additional training samples and given the ground-truth measurement of zero. Alternatively, one may use so-called known Adversarial Training technique in order to ensure that such examples cannot be differentiated by the system. A similar approach can be used, in some examples, to include different image reconstruction protocols and images from multiple scanners.

Accounting for Misalignment Between the Location ROIs

It may be the case that the ROIs between images vary in accuracy when the system is used to predict change in clinical practice. If the ROIs are being placed manually, the user may want only to place them very approximately. An automated ROI placement may be sensitive to unforeseen variations in the imaging protocol.

Advantageously, in accordance with some examples of the invention, the direct quantification system may be trained to be robust to such variations by providing random shifts to the ROI/location during training. Here, for example for each pair of training examples, the ROI may be shifted around and used multiple times during training. In this manner, the system will learn to produce the same output regardless of the exact placement of the ROIs.

Outputting Values and Change

In some situations, it may be desirable to output a change measurement and measurements simultaneously. For example, as well as predicting the change in a volume of a lesion, examples of the invention may be configured to additionally output the volume data. This may be useful for some applications where the actual measurement as well as its change is relevant for clinical decision making. Examples of the invention may also be adapted to produce multiple outputs by adjusting the loss function, say in 814 of FIG. 8, such that both the absolute values of the measurements and the changes in measurements are accounted for. Providing multiple outputs from CNN regression is known from the art and requires adding parallel layers to support this. Another advantage of this approach is that the user may inspect the values for consistency as a means to ensure that the change measurements are accurate.

Thus, examples of the further aspect of the invention propose a quantification system that includes: at least one input configured to provide two input medical images and two locations of interest in said input medical images that correspond to a same anatomical region; and a mapping circuit configured to compute a direct quantification of change of said input medical images from the at least one input.

Some examples of the further aspect of the invention propose a quantification system that include a direct change estimation technique that receives at least two input medical images and identifies at least one region of interest related to the same structure from the at least two input medical images, and derive an estimate of change from the at least two medical images by processing the at least two medical images with equivalent images for which a ground-truth describing the change is known.

Thus, examples of the further aspect of the invention propose a direct volume estimation technique that performs a direct quantification assessment of at least two input medical images and at least one region of interest input to produce direct quantification result, wherein, in an absence of quantitative measures, the direct quantification assessment uses training data that has been ranked to produce measurements of change between the at least two input medical images directly.

In some examples, the at least two input medical images may be of the same patient over time or between different patients in case of a general assessment of change.

In some examples, the known ground-truth describing the change can be derived from either a estimation of change from computed measurement from each image at each region and each time point at each change or a direct assessment of change.

In some examples, the training data encompasses quantifying changes in Ground Glass Opacities (GGOs) over a pair of images taken over time.

In particular, some examples of the invention further support partial ground-truth measurements to be additionally used in creating the training data.

Some examples of the invention utilise change data carried out over a short period of time, e.g. of an order of seconds or minutes to calibrate the direct quantification system that is creating the training data to recognise changes that are not clinically relevant or important.

Some examples of the invention provide the option to select either: changing a loss function measuring a prediction error such that where change measurements are available with particular examples in the training data then the loss function calculates an error based on that; and where only ranking data is available then it uses a loss function based on that only.

In particular, some examples of the invention describe a direct quantification assessment that uses a mapping circuit, which in this example is at least one of: a regression circuit applying a regression algorithm, a classifier circuit applying a multi-way classification algorithm.

Some examples of the invention also support a location of interest input to be taken into account by the direct quantification assessment, which may be specified in a number of ways, but may include a single point or region of interest (ROI) provided by the user or an automated detection algorithm. When ROI is employed, an approximate area of the image that is of interest to the user is provided to the system but this will not be a detailed segmentation of the anatomical object of interest.

In some examples, the output of the direct quantification system may include both a prediction of a change in a volume of a lesion, as well as an output of the raw volume data.

Although examples of the invention have been described with reference to the direct quantification system using a Convolutional Neural Network for the regression algorithm, it is envisaged that the concepts described herein may be used with Random Forest, or a Support Vector Machine for classification.

Although examples of the invention have been described with reference to an interpretation of medical images in a clinical setting e.g. in radiology, cardiology, oncology, it is envisaged that in other examples, the concepts described herein may be employed, say, within a clinical trial for a medical intervention e.g. drug, radiation therapy, etc.

In some examples, the quantification system may be provided as an integrated tool within a broader class of software devices such as a Picture Archiving Communications System, Advanced Visualisation software package or Modality Workstation/Processing software.

The present invention has been described with reference to the accompanying drawings. However, it will be appreciated that the present invention is not limited to the specific examples herein described and as illustrated in the accompanying drawings. Furthermore, because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

The invention may be implemented in a computer program for running on a computer system, at least including code portions for performing steps of a method according to the invention when run on a programmable apparatus, such as a computer system or enabling a programmable apparatus to perform functions of a device or system according to the invention.

A computer program is a list of instructions such as a particular application program and/or an operating system. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system.

Therefore, some examples describe a non-transitory computer program product having executable program code stored therein for training a computer aided risk assessment, the program code operable for quantifying a medical image, the method comprising: providing at least one input medical image and at least a second input that provides a location of interest of the at least one input medical image; computing a direct quantification result from the location of interest of the at least one input medical image to a quantification of interest and output a direct first quantification result therefrom; generating a saliency map as part of the computation of the direct quantification result; and deriving a segmentation from the saliency map, such that the segmentation independently generates a second quantification result that is within a result range of the direct first quantification result.

The computer program may be stored internally on a tangible and non-transitory computer readable storage medium or transmitted to the computer system via a computer readable transmission medium. All or some of the computer program may be provided on computer readable media permanently, removably or remotely coupled to an information processing system. The tangible and non-transitory computer readable media may include, for example and without limitation, any number of the following: magnetic storage media including disk and tape storage media; optical storage media such as compact disk media (e.g., CD-ROM, CD-R, etc.) and digital video disk storage media; non-volatile memory storage media including semiconductor-based memory units such as FLASH memory, EEPROM, EPROM, ROM; ferromagnetic digital memories; MRAM; volatile storage media including registers, buffers or caches, main memory, RAM, etc.

A computer process typically includes an executing (running) program or portion of a program, current program values and state information, and the resources used by the operating system to manage the execution of the process. An operating system (OS) is the software that manages the sharing of the resources of a computer and provides programmers with an interface used to access those resources. An operating system processes system data and user input, and responds by allocating and managing tasks and internal system resources as a service to users and programs of the system.

The computer system may for instance include at least one processing unit, associated memory and a number of input/output (I/O) devices. When executing the computer program, the computer system processes information according to the computer program and produces resultant output information via I/O devices.

In the foregoing specification, the invention has been described with reference to specific examples of embodiments of the invention. It will, however, be evident that various modifications and changes may be made therein without departing from the scope of the invention as set forth in the appended claims and that the claims are not limited to the specific examples described above.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures can be implemented which achieve the same functionality.

Any arrangement of components to achieve the same functionality is effectively 'associated' such that the desired functionality is achieved. Hence, any two components herein combined to achieve a particular functionality can be seen as 'associated with' each other such that the desired functionality is achieved, irrespective of architectures or intermediary components. Likewise, any two components so associated can also be viewed as being 'operably connected,' or 'operably coupled,' to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms 'a' or 'an,' as used herein, are defined as one, or more than one. Also, the use of introductory phrases such as 'at least one' and 'one or more' in the claims should not be construed to imply that the introduction of another claim element by the indefinite articles 'a' or 'an' limits any particular claim containing such introduced claim element to inventions containing only one such element, even when the same claim includes the introductory phrases 'one or more' or 'at least one' and indefinite articles such as 'a' or 'an.' The same holds true for the use of definite articles. Unless stated otherwise, terms such as 'first' and 'second' are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

The invention claimed is:

1. A quantification system comprising:
   at least one input configured to provide at least one input medical image and provide a location of interest in the at least one input medical image, where the location of interest is associated with a region of interest;
   a mapping circuit configured to:
     compute a direct quantification result from intensities within the region of interest of the at least one input medical image to a quantification of interest and output a direct first quantification result therefrom; and
     generate a saliency map as part of the computation of the direct first quantification result; and
     derive a segmentation from the saliency map, such that the segmentation independently generates a second quantification result that is within a result range of the direct first quantification result.

2. The quantification system of claim 1, wherein the mapping circuit being configured to compute a direct quantification result is at least one of: a regression circuit configured to apply a regression algorithm, a classifier circuit configured to apply a classification algorithm.

3. The quantification system of claim 2, wherein the location of interest input comprises a single point of interest, provided by an user or an automated detection algorithm.

4. The quantification system of claim 1, wherein the mapping circuit is configured to obtain an implicit segmentation using a first set of voxels of the at least one medical image that is identified as being more important than a second set of voxels of the at least one medical image in the computation.

5. The quantification system of claim 4, wherein the mapping circuit is configured to map input voxels from the at least one medical image to a quantification of interest output value through a linear function, or series of non-linear function(s).

6. The quantification system of claim 1, wherein the mapping circuit is configured to perform an additional mapping operation that modifies the saliency map such that the additional mapping generates an implicit segmentation that is consistent with the direct first quantification result.

7. The quantification system of claim 6, wherein the additional mapping operation employs a threshold when it independently generates the second quantification result, where the threshold is employed if a binary segmentation is used or, in an application of non-linear weighting, real valued non-binary segmentation is used.

8. The quantification system of claim 1, wherein the mapping circuit is configured to allow a user to make adjustments to the derived segmentation that improves an accuracy of the direct first quantification result.

9. The quantification system of claim 2, wherein the regression circuit uses a Convolutional Neural Network.

10. The quantification system of claim 2, wherein the classifier circuit uses a Random Forest, or a Support Vector Machine, for classification.

11. The quantification system of claim 1, wherein the mapping circuit is employed in at least one of:
an interpretation of medical images in a clinical setting, in one or more of: radiology, cardiology, oncology;
a clinical trial for a medical intervention for drug or radiation therapy.

12. The quantification system of claim 1, wherein the quantification system comprises a part of at least one from a group of: a picture archiving communications system, an advanced visualisation software package, a modality workstation.

13. The quantification system of claim 1, wherein the at least one input comprises a first input configured to provide at least one input medical image and a second input that provides the region of interest of the at least one input medical image.

14. A method of quantifying a medical image, the method comprising:
providing at least one input medical image and at least a second input that provides a location of interest of the at least one input medical image, where the location of interest is associated with a region of interest;
computing a direct quantification result from intensities within the region of interest of the at least one input medical image to a quantification of interest and output a direct first quantification result therefrom;
generating a saliency map as part of the computation of the direct quantification result; and
deriving a segmentation from the saliency map, such that the segmentation independently generates a second quantification result that is within a result range of the direct first quantification result.

15. The method of quantifying a medical image of claim 14, wherein generating a saliency map comprises at least one of: applying a regression algorithm, applying a classification algorithm.

16. The method of quantifying a medical image of claim 14, wherein generating a saliency map as part of the computation of the direct quantification result comprises obtaining an implicit segmentation using a first set of voxels of the at least one medical image that is identified as being more important than a second set of voxels of the at least one medical image in the computation.

17. The method of quantifying a medical image of claim 16, wherein generating a saliency map as part of the computation of the direct quantification result comprises mapping input voxels from the at least one medical image to a quantification of interest output value through a linear function, or series of non-linear function(s).

18. The method of quantifying a medical image of claim 14, wherein generating a saliency map as part of the computation of the direct quantification result comprises performing an additional mapping operation that modifies the saliency map such that the additional mapping function generates an implicit segmentation that is consistent with the direct first quantification result.

19. The method of quantifying a medical image of claim 18, wherein performing an additional mapping operation comprises employing a threshold when it independently generates the second quantification result, where the threshold is employed if a binary segmentation is used or in an application of non-linear weighting real valued non-binary segmentation is used.

20. The method of quantifying a medical image of claim 18, wherein generating a saliency map as part of the computation of the direct quantification result comprises allowing a user to adjust the derived segmentation that improves an accuracy of the direct quantification result.

* * * * *